United States Patent [19]

Higel et al.

[11] Patent Number: 5,097,041

[45] Date of Patent: Mar. 17, 1992

[54] PURIFICATION OF 2-ARYL-2H-BENZOTRIAZOLES

[75] Inventors: Ariane Higel, Rixheim, France; Sebastian Stäubli, Magden, Switzerland; Daniel Thibaut, Michelbach-le-Bas, France; Hans Horisberger, Muttenz, Switzerland

[73] Assignee: Ciba-Geigy Corporation, Ardsley, N.Y.

[21] Appl. No.: 595,917

[22] Filed: Oct. 11, 1990

[30] Foreign Application Priority Data

Oct. 19, 1989 [CH] Switzerland ............... 3800/89

[51] Int. Cl.$^5$ ............................. C07D 249/20
[52] U.S. Cl. .............................. 548/260; 548/259; 548/261
[58] Field of Search ............... 548/257, 259, 260, 261

[56] References Cited

U.S. PATENT DOCUMENTS

| | | | |
|---|---|---|---|
| 3,184,471 | 5/1965 | Harder | 548/257 |
| 3,334,054 | 8/1967 | Howard | 548/257 |
| 3,794,493 | 2/1974 | Sobel et al. | |
| 4,041,044 | 8/1977 | White | 548/257 |
| 4,127,586 | 11/1978 | Rody et al. | 548/259 |
| 4,141,903 | 2/1979 | Adler | 548/260 |
| 4,153,565 | 5/1979 | Braid | 548/257 |
| 4,219,480 | 8/1980 | White et al. | 546/260 |
| 4,230,867 | 10/1980 | Kintopf et al. | 548/260 |
| 4,447,614 | 5/1984 | Beschke et al. | |
| 4,611,061 | 9/1986 | Beard et al. | 548/259 |
| 4,675,352 | 6/1987 | Winter et al. | 548/257 |
| 4,785,063 | 11/1988 | Slongo et al. | 548/260 |
| 4,853,471 | 8/1989 | Rody et al. | 548/260 |
| 4,891,396 | 1/1990 | Ajar et al. | 548/259 |
| 4,921,966 | 5/1990 | Stegmann | 548/260 |
| 5,003,076 | 3/1991 | Narita et al. | 548/257 |

OTHER PUBLICATIONS

Kapisinska et al., Chem. Prum., vol. 21, No. 3, pp. 129–134 (1971).
Derwent Abst. 76-90928x/49.
Derwent Abst. 76-90565x/49.
Kapisinska et al. Chem. Abstr., vol. 74, Entry 125570v.

Primary Examiner—Donald G Daus
Attorney, Agent, or Firm—Luther A. R. Hall

[57] ABSTRACT

There is disclosed a process in which a melt of a 2-aryl-2H-benzotriazole containing colored contaminants, or a solution thereof in an organic nonpolar solvent, is purified by treatment with a strongly acidic synthetic cationic exchange resin.

18 Claims, No Drawings

PURIFICATION OF 2-ARYL-2H-BENZOTRIAZOLES

The present invention relates to an improved process for purifying 2-aryl-2H-benzotriazoles.

2-Aryl-2H-benzotriazoles have long been used as UV absorbers in plastics, paints or other materials. When synthesised, they are usually coloured. A high degree of purity is required for the above utilities, especially the absence of coloured contaminants. 2-Aryl-2H-benzotriazoles must therefore as a rule be subjected to additional purification, for example by crystallisation, distillation or extraction. A combination of these methods is usually necessary to attain the desired degree of purity. This entails additional process steps and hence additional energy, raw material and disposal costs.

There has now been found an improved process for removing coloured contaminants from 2-aryl-2H-benzotriazoles. The novel process is based on the observation that a selected type of ion exchanger in a nonpolar environment of the ion exchanging groups can be used as adsorbent for the coloured contaminants. Under these conditions, the removal of the coloured contaminants proceeds virtually without any occurrence of ion exchange. The desorption of the contaminants after the purification operation can subsequently be effected by a change in the polarity of the environment of the ion exchanging groups by regenerating the ion exchange resin with a polar solvent.

The novel purification process is distinguished by a low consumption of adsorbent. Further, the adsorbent can be regenerated periodically. The exhausted adsorbent can be completely incinerated, so that no waste disposal problems arise. Moreover, the purification process can be carried out with solvents which can also be used for the synthesis of 2-aryl-2H-benzotriazoles. These solvents can be returned to the process. A further advantage is the improved quality of the purified product, so that a direct isolation without crystallisation steps is possible. Quite generally, the novel purification substantially reduces environmental pollution.

The present invention relates to a process for purifying 2-aryl-2H-benzotriazoles which contain coloured contaminants. The process comprises treating a melt of a 2-aryl-2H-benzotriazole, or a solution thereof in an organic nonpolar solvent, with a synthetic cationic ion exchange resin which contains strongly acidic groups at least some of which are in protonated form.

The 2-aryl-2H-benzotriazoles used in the process of this invention may quite generally be unsubstituted or substituted 2H-benzotriazoles which carry an aryl radical, preferably a phenyl radical, in 2-position. Preferably they are unsubstituted or substituted 2-(2-hydroxyphenyl)-2H-benzotriazoles, more particularly compounds of formula I

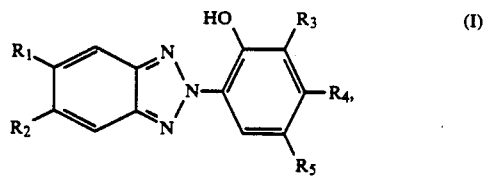

wherein $R_1$ is hydrogen, chloro or $C_1$-$C_{12}$alkyl, $R_2$ is hydrogen, chloro, $C_1$-$C_{12}$alkyl, $C_1$-$C_4$alkoxy, $C_2$-$C_9$alkoxycarbonyl, $C_7$-$C_9$phenylalkyl, carboxyl or —$SO_3H$, $R_3$ is hydrogen, chloro, $C_1$-$C_{12}$alkyl, cycloalkyl containing 5 or 6 ring carbon atoms, phenyl, phenyl which is substituted by $C_1$-$C_8$alkyl, or $C_7$-$C_9$phenylalkyl, $R_4$ is hydrogen, chloro, $C_1$-$C_4$alkyl, $C_1$-$C_4$alkoxy or hydroxyl, and $R_5$ is $C_1$-$C_{12}$alkyl, $C_1$-$C_4$alkoxy, cycloalkyl containing 5 or 6 ring carbon atoms, phenyl, phenyl which is substituted by $C_1$-$C_8$alkyl, chloro, $C_7$-$C_9$phenylalkyl or —$C_nH_{2n}$—$COOR_6$, n is an integer from 0 to 4 and $R_6$ is hydrogen or $C_1$-$C_{12}$alkyl.

Such compounds are disclosed, for example, in U.S. Pat. No. 4,041,044 or in European patent application 0 57 160. 2-Aryl-2H-benzotriazoles can be prepared, for example, by reductive cyclisation of o-nitroazobenzenes which can in turn be obtained by diazotisation of o-nitroanilines and reaction with suitable coupling components. Such reactions are disclosed, for example, in U.S. Pat. No. 4,041,044 or in European patent application 0 57 160, and in GB patent specifications 1 494 824, 1 494 825 and 1 494 826. What is disclosed in these references also falls within the scope of this invention.

In the practice of this invention it is preferred to purify compounds of formula I, wherein $R_1$ is hydrogen, chloro or $C_1$-$C_{12}$alkyl, preferably hydrogen or chloro, $R_2$ is hydrogen, $R_3$ is hydrogen, $C_1$-$C_{12}$alkyl or phenyl-$C_1$-$C_3$alkyl, preferably α,α-dimethylbenzyl, $R_4$ is hydrogen, $R_5$ is $C_1$-$C_{12}$alkyl, preferably $C_1$-$C_8$alkyl, phenyl-$C_1$-$C_3$alkyl, preferably α,α-dimethylbenzyl, or a group —$C_2H_4$—$COOR_6$, and $R_6$ is hydrogen or $C_1$-$C_{12}$alkyl, preferably $C_1$-$C_8$alkyl and, most preferably, hydrogen or $C_1$-$C_5$alkyl.

In the practice of this invention it is especially preferred to purify compounds of formula I, wherein $R_1$ is hydrogen or chloro, $R_2$ is hydrogen, $R_3$ is hydrogen or $C_1$-$C_8$alkyl, $R_4$ is hydrogen, and $R_5$ is $C_1$-$C_8$alkyl.

The nature of the coloured contaminants is not known. They are present in the crude product in insignificant amounts, typically less than 1%, based on the crude product. The removal of these contaminants from the solution or melt can be monitored by routine methods, for example by observing the transmission of the contaminated or purified solution or melt at a selected wavelength.

The cationic exchange resins used in the process of this invention must contain strongly acidic groups and at least some of these groups must be in protonated form.

Exemplary of strongly acidic groups are sulfonic acid groups or exchanger groups of comparable or stronger acidity. The strongly acidic groups are preferably sulfonic acid groups.

The adsorptive capacity of the cationic exchange resin employed depends, inter alia, on the amount of protonated exchanger groups available to the material which it is desired to purify cationic exchange resins having a large surface area and a high percentage of exchanger groups will therefore conveniently be chosen. The cationic exchange resins employed will normally have a surface area greater than 40 m²/g (measured by the BET method).

Strongly acidic macroporous synthetic cationic exchange resins are preferred.

The term "macroporous" is familiar to the skilled person and denotes a synthetic resin whose pores are already contained in the resin in the unswollen state and are not, or not exclusively, formed by swelling. These ion exchangers have a large surface, usually greater than 40 m²/g (measured by the BET method), and they are porous. The average pore size is normally smaller than 7000 nm. The average pore size is preferably from 2000° to 7000 nm.

It is, however, also possible to use cationic exchange resins in finely particulate form so as to obtain a large surface area.

Particuarly preferred cationic exchange resins are sulfonic acid group containing macroporous cationic exchange resins which are based on polystyrene and which are crosslinked with an amount of divinyl benezene sufficient to form the macrocyclic structure.

Exemplary of such macroporous ion exchangers are the products Lewatite ® 2641, Lewatite ® 2661 and Lewatite ® 2611 sold by Bayer, Amberlyst ® 15, Amberlyst ® N-1010 and Amberlite ® 200 sold by Rohm & Haas, and Dowex ® MSC-1, sold by Dow Chemicals.

The ion exchange resins can be used in any desired form, for example in the form of membranes, fibres or, preferably, in granular form.

At least some of the acid groups of the cationic exchange resin must be in protonated form. The number of protonated acid groups sufficient for the individual case can be determined by the skilled person by routine experimentation, as the purifying effect increases with the number of accessible protonated groups.

Preferably almost all acid groups of the cationic exchange resin will be in protonated form.

The purifying effect is also influenced, inter alia, by the polarity of the solvent employed. Experiments have shown that a satisfactory purifying effect is not achieved with polar solvents, for example alcohols.

The nonpolar organic solvent may not contain any groups which cause exchange with the protonated acid groups in the cationic exchange resin and it should normally have a polarity $E_T^N$ of less than 0.30. $E_T^N$ is an empirical solvent parameter which is derived from the solvatochromism of a pyridinium-N-phenoxide betaine. Particulars relating thereto are described by Ch. Reichert in "Solvents and Solvent Effects in Organic Chemistry", pp. 407–411, Verlagsgesellschaft VCh (1988).

Representative examples of suitable organic nonpolar organic solvents are aliphatic or aromatic hydrocarbons which may be halogenated and which are liquid at room temperature, or aliphatic ethers.

Exemplary of suitable aliphatic hydrocarbons are n-hexane, n-octane, petroleum ether, cyclohexane or methylcyclohexane. Exemplary of suitable aromatic hydrocarbons are benzene, toluene, xylene or mesitylene. Exemplary of suitable halogenated hydrocarbons are dichloromethane, chloroform, trichloroethane, tetrachloroethane, chlorobenzene or dichlorobenzene. Exemplary of suitable aliphatic ethers are diethyl ether, dibutyl ether, tetrahydrofuran or dioxane.

It is also possible to use nonpolar organic solvents.

It is particularly preferred to use aromatic hydrocarbons which are liquid at room temperature, most preferably toluene or xylene.

The 2-aryl-2H-benzotriazole to be purified can be in the form of a solution in a nonpolar organic solvent or of a melt.

Depending on the synthesis of the 2-aryl-2H-benzotriazole, the solution or melt to be purified may contain, in addition to the solvent and the coloured contaminants, solid contaminants, especially undissolved or only partially dissolved salts such as sodium sulfate. Salts may interfere with the removal of the coloured contaminants, as an ion exchange occurs, so that on the one hand the solution or melt to be purified is acidified and, on the other, the protonated form of the acid radicals in the cationic exchange resin is consumed, usually resulting in a lowering of the adsorptive capacity or even in loss of the purifying effect.

In a preferred embodiment of the process of this invention, a solution of the contaminated 2-aryl-2H-benzotriazole in an organic nonpolar solvent is clarified by filtration, prior to treatment with the cationic exchange resin, to remove solid or partially dissolved salts.

This is accomplished conveniently by treating the starting solution in a manner known per se with a filter aid, for example with cellulose or, preferably, with activated charcoal, and filtering the solution.

The process of this invention can be carried out batchwise or, preferably, continuously.

Process parameters, such as the amount of cationic exchange resin, the duration of the treatment of the contaminated solution or melt with the cationic exchange resin and the temperature of the solution or melt to be purified, are essentially not critical for carrying out the process of the invention. These parameters are chosen such that the desired degree of purification is achieved. Optimisation of these parameters is known per se to the skilled person. The upper temperature range of the process will normally be governed by the decomposition temperature of the cationic exchange resin, whereas the lower temperature range is usually predetermined by the solidification temperature of the melt or solution to be purified.

The purification can be carried out under atmospheric or elevated pressure. It is preferably carried out under atmospheric pressure.

In batchwise operation, the melt or solution to be purified is normally put into a reactor which contains the cationic exchange resin. If a solution is to be purified, then the cationic exchange resin will normally be charged to the reactor together with an organic nonpolar solvent, preferably with the same solvent which the solution to be purified also contains. After the desired degree of purification of the solution has been attained, the cationic exchange resin is removed, for example by filtration.

In continuous operation, the cationic exchange resin is normally charged to an exchange column. As a rule the column will contain an organic nonpolar solvent in addition to the cationic exchange resin, preferably the same solvent which the solution to be purified also contains. A number of exchange columns can also be connected in series.

In a preferred embodiment of the process of this invention, the melt or solution containing the contaminated 2-aryl-2H-benzotriazole is passed through at least one exchange column, preferably through two exchange columns connected in series which contain the cationic exchange resin in a form suitable for column purification, for example in granular form, such as in the form of beads or pellets.

In a particularly preferred embodiment of the present invention, two exchange columns are connected in series and the eluate from the first column is observed, for example by monitoring the transmission of the solution at a selected wavelength. If the adsorptive capacity of the first column is exhausted, then the column is removed for regeneration. Virtually without interruption of the purifying operation, a fresh column can then be connected to the original second column or the original second column is used as first column and a fresh second column is connected to it.

The flow rate through an exchange column is normally 0.5 to 30 bed volumes/h, preferably 1 to 6 bed volumes/h.

The purified 2-aryl-2H-benzotriazole is usually isolated by evaporating the solvent. A further purification, for example by crystallisation or by distillation, is generally no longer necessary. If necessary, the product obtained is comminuted, for example by grinding.

In a particularly preferred variant of the process of the invention, the solvent is evaporated in a fluidised bed granulator, a spray drier or in a combination of both devices. In this process variant, the product is obtained direct in a ready for use, flowable and non-dusty form.

The regeneration of the exhausted ion exchange resin can be effected in simple manner by a change in the polarity of the solvent. The steps of the regeneration depend substantially on whether the exhausted ion exchange resin is essentially still in protonated form and is therefore to be regenerated by a simple desorption of the contaminants, or whether an ion exchange has occurred at the bulk of the acid groups, for example as a consequence of the presence of salts in the solution to be purified so that the simple desorption of the contaminants will not suffice to produce a sufficient purifying effect.

The regeneration of the cationic exchange resin, which is substantially in protonated form, comprises the following steps:

i) washing the loaded cationic exchange resin with an organic nonpolar solvent until almost the entire 2-aryl-2H-benzotriazole adsorbed thereon is removed, ii) effecting desorption of the contaminants on the cationic exchange resin by treatment with a polar solvent or with a mixture containing a nonpolar and a polar solvent, preferably with an organic polar solvent, or with a mixture containing an organic nonpolar and an organic polar solvent in which the adsorbed compounds are sufficiently soluble, and iii) expelling the polar solvent with an organic nonpolar solvent.

The regeneration of the cationic exchange resin which is substantially in non-protonated form comprises the following steps:

iv) washing the loaded cationic exchange resin with an organic nonpolar solvent until almost the entire 2-aryl-2H-benzotriazole adsorbed thereon is removed, v) effecting desorption of the contaminants on the cationic exchange resin by treatment with a polar solvent or with a mixture containing a nonpolar and a polar solvent, preferably with an organic polar solvent, or with a mixture containing an organic nonpolar and an organic polar solvent in which the adsorbed compounds are sufficiently soluble, vi) regenerating the protonated form of the cationic exchanger by treatment with an acid, and vii) expelling the polar solvent and the acid with an organic nonpolar solvent.

Steps v) and vi) can also be carried out simultaneously.

Exemplary of suitable polar solvents for the desorption step are alcohols, phenols or carboxylic acids.

It is especially preferred to use alcohols, most preferably monohydric aliphatic alcohols such as methanol, ethanol, propanol, butanol, pentanol or hexanol.

In the desorption step it is most particularly preferred to use a mixture of the organic nonpolar solvent which has been used in the adsorption step and an organic polar solvent.

If the non-protonated form of the cationic exchange resin is to be regenerated, then it is preferred to use a monohydric aliphatic alcohol in which a sulfonic acid, for example p-toluenesulfonic acid, is dissolved.

In a most particularly preferred variant of the process of this invention, the organic nonpolar solvent used for the solution of the 2-aryl2H-benzotriazole to be purified and in steps i), iii), iv) and vii) and, if appropriate, in steps ii) and v), is an aromatic hydrocarbon, preferably xylene or toluene, and the polar solvent used in steps ii) and v) is a monohydric aliphatic alcohol, preferably butanol. In steps ii) and v) it is most preferred to use a mixture of xylene and 2-butanol.

The invention is illustrated by the following Examples.

EXAMPLE 1

Purification of

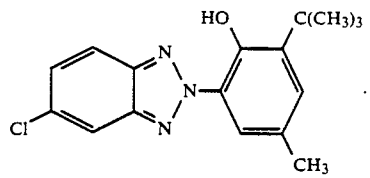

A very darkly coloured solution containing 40% by weight, based on said solution, of 2-(2-hydroxy-3-tert-butyl-5-methylphenyl)-2H-5-chlorobenzotriazole in xylene (amount of coloured contaminants <1% by weight) is clarified by filtration over activated charcoal at 85° C. and then passed through two exchange columns connected in series and containing Amberlyst ® 15. The flow rate through a column is 2 bed volumes/h. The solution passing out from the second column is almost colourless.

The quality of the purified solution is monitored at the exit of the first and of the second column. The increased loading of the first column leads in the course of the purification to a decrease in quality, which is compensated for by the second column. When the adsorptive capacity of the first column is exhausted, the column is replaced and the loaded ion exchange resin is regenerated.

EXAMPLE 2

Regeneration of the Loaded Ion Exchange Resin

The loaded ion exchange resin of Example 1 is regenerated in a 3-step process. First, the column is washed with xylene at 85° C. to remove 2-hydroxyaryl-2H-benzotriazole. Then desorption of the coloured contaminants is effected by eluting the column with a mixture of xylene and 2-butanol (20:80 parts by volume). When the eluate is almost colourless, the column is washed with xylene at 70° C. to expel the polar solvent. The column can then be reused for the purification process.

EXAMPLE 3

Purification of

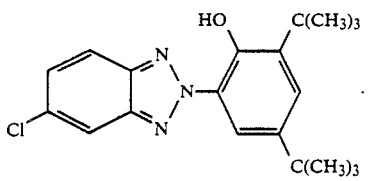

A very darkly coloured solution containing 50% by weight, based on said solution, of 2-(2-hydroxy-3,5-di-tert-butylphenyl)-2H-5-chlorobenzotriazole in xylene is clarified by filtration as in Example 1 and purified through two columns connected in series and containing Amberlyst® 15. The flow rate of the solution through a column is 2 bed volumes/h. The solution passing out from the second column is almost colourless.

EXAMPLE 4

Purification of

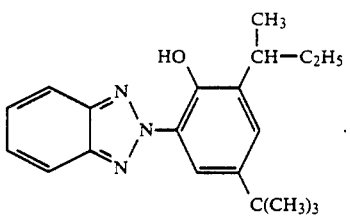

A very darkly coloured solution containing 50% by weight, based on said solution, of 2-(2-hydroxy-3-isobutyl-5-tert-butylphenyl)-2H-benzotriazole in xylene is clarified by filtration as in Example 1 and purified through two columns connected in series and containing Amberlyst® 15. The flow rate of the solution through a column is 1 bed volume/h. The solution passing out from the second column is almost colourless.

EXAMPLE 5

Purification of

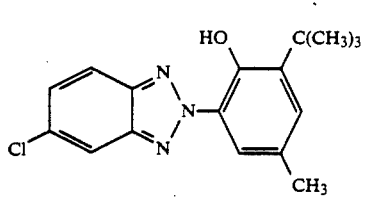

without prior clarifying f

The procedure of Example 1 is repeated without prior clarifying over activated charcoal. After passage through the exchange columns, the originally very darkly coloured solution of 2-(2-hydroxy-3-tert-butyl-5-methylphenyl)-2H-5-chlorobenzotriazole is almost colourless.

EXAMPLE 6

Purification of

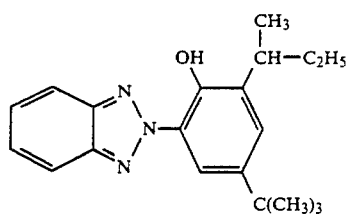

as melt

The procedure described in Example 4 is carried out at 90° C. with or without prior clarifying filtration over activated charcoal. After passage through the exchange columns, the originally very darkly coloured melt of 2-(2-hydroxy-3-isobutyl-5-tert-butylphenyl)-2H-benzotriazole is decolourised.

What is claimed is:

1. A process for purifying a 2-aryl-2H-benzotriazole of formula I

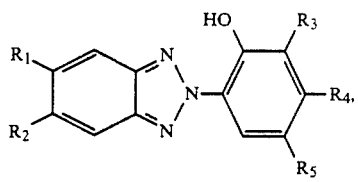

wherein $R_1$ is hydrogen, chloro or $C_1$-$C_{12}$alkyl, $R_2$ is hydrogen, chloro, $C_1$-$C_{12}$alkyl, $C_1$-$C_4$alkoxy, $C_2$-$C_9$alkoxycarbonyl, $C_7$-$C_9$phenylalkyl, carboxy or —$SO_3H$, $R_3$ is hydrogen, chloro, $C_1$-$C_{12}$alkyl, cycloalkyl of 5 to 6 carbon atoms, $C_7$-$C_9$phenylalkyl, phenyl or said phenyl substituted by $C_1$-$C_8$alkyl, $R_4$ is hydrogen, chloro, $C_1$-$C_4$alkyl, $C_1$-$C_4$alkoxy or hydroxyl, and $R_5$ is $C_1$-$C_{12}$alkyl, $C_1$-$C_4$alkoxy, cycloalkyl of 5 to 6 carbon atoms, phenyl, said phenyl substituted by $C_1$-$C_8$alkyl, or $R_5$ is chloro, $C_7$-$C_9$phenylalkyl or —$C_nH_{2n}$—$COOR_6$ where n is an integer from 0 to 4 and $R_6$ is hydrogen or $C_1$-$C_{12}$alkyl, which contains colored contaminants, which process comprises treating a melt of a compound of formula I, or a solution thereof in an organic nonpolar solvent, with a synthetic cationic ion exchange resin which contains strongly acidic sulfonic acid groups at least some of which are in protonated form.

2. A process according to claim 1, wherein the cationic exchange resin is a strongly acidic macroporous synthetic cationic exchange resin.

3. A process according to claim 2, which comprises the use of a sulfonic acid group containing macroporous cationic exchange resin which is based on polystyrene and which is crosslinked with an amount of divinylbenzene sufficient to form the macrocyclic structure.

4. A process according to claim 1, wherein the organic nonpolar solvent used is an aromatic hydrocarbon which is liquid at room temperature.

5. A process according to claim 4 wherein the solvent is toluene or xylene.

6. A process according to claim 1, wherein a solution containing the contaminated 2-aryl-2H-benzotriazole in an organic nonpolar solvent is clarified by filtration prior to the treatment with the cationic exchange resin to remove solid or partially dissolved salts.

7. A process according to claim 6, wherein the clarifying filtration is carried out by treating the solution with activated charcoal.

8. A process according to claim 1, wherein the melt or solution containing the contaminated 2-aryl-2H-benzotriazole is passed through at least one exchange column, which contains the cationic exchange resin in granular form.

9. A process according to claim 4 where there are two exchange columns which are connected in series.

10. A process according to claim 9, wherein the flow rate through the exchange column is 1 to 6 bed volumes/h.

11. A process according to claim 1, wherein the solution of the 2-aryl-2H-benzotriazole in a nonpolar organic solvent is isolated after purification through the cationic exchange resin by evaporating the solvent.

12. A process according to claim 11, wherein the evaporation of the solvent is carried out in a fluidised bed granulator, a spray drier or in a combination of both devices.

13. A process according to claim 1, wherein the cationic exchange resin in substantially protonated form is regenerated after exhaustion of the adsorptive capacity, comprising the steps of:
   i) washing the loaded cationic exchange resin with an organic nonpolar solvent until almost the entire 2-aryl-2H-benzotriazole adsorbed thereon is removed,
   ii) effecting desorption of the contaminants on the cationic exchange resin by treatment with a polar solvent or with a mixture containing a nonpolar and a polar solvent, in which the adsorbed compounds are sufficiently soluble, and
   iii) expelling the polar solvent with an organic nonpolar solvent.

14. A process according to claim 13 wherein the organic nonpolar solvent used for the solution of the 2-aryl-2H-benzotriazole and in steps i), iii), iv) and vii) and, where appropriate, in steps ii) and v), is an aromatic hydrocarbon, and the polar solvent used in steps ii) and v) is a monohydric aliphatic alcohol.

15. A process according to claim 14 where the nonpolar solvent is xylene or toluene and the polar solvent is butanol.

16. A process according to claim 1, wherein the cationic exchange resin in substantially non-protonated form is regenerated after exhaustion of the adsorptive capacity, comprising the steps of:
   iv) washing the loaded cationic exchange resin with an organic nonpolar solvent until almost the entire 2-aryl-2H-benzotriazole adsorbed thereon is removed,
   v) effecting desorption of the contaminants on the cationic exchange resin by treatment with a polar solvent or with a mixture containing a nonpolar and a polar solvent, in which the adsorbed compounds are sufficiently soluble,
   vi) regenerating the protonated form of the cationic exchange resin by treatment with an acid, and
   vii) expelling the polar solvent and the acid with an organic solvent.

17. A process according to claim 1 where the nonpolar solvent is xylene or toluene and the polar solvent is butanol.

18. A process according to claim 16 wherein the organic nonpolar solvent used for the solution of the 2-aryl-2H-benzotriazole and in steps i), iii), iv) and vii) and, where appropriate, in steps ii) and v), is an aromatic hydrocarbon, and the polar solvent used in steps ii) and v) is a monohydric aliphatic alcohol.

* * * * *